United States Patent
Trieu

(10) Patent No.: US 8,221,428 B2
(45) Date of Patent: Jul. 17, 2012

(54) SACRO-ILIAC JOINT IMPLANT SYSTEM, METHOD AND INSTRUMENT

(75) Inventor: Hai H. Trieu, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 262 days.

(21) Appl. No.: 12/694,095

(22) Filed: Jan. 26, 2010

(65) Prior Publication Data

US 2011/0184519 A1  Jul. 28, 2011

(51) Int. Cl.
*A61B 17/70* (2006.01)
(52) U.S. Cl. ...................... 606/86 A; 606/104
(58) Field of Classification Search .................. 606/246, 606/86 A, 96, 99, 104; 623/17.11
See application file for complete search history.

(56) References Cited

U.S. PATENT DOCUMENTS

| | | | |
|---|---|---|---|
| 6,053,916 A | 4/2000 | Moore | |
| 6,620,196 B1 | 9/2003 | Trieu | |
| 6,733,531 B1 | 5/2004 | Trieu | |
| 6,893,466 B2 | 5/2005 | Trieu | |
| 6,899,719 B2 | 5/2005 | Reiley et al. | |
| 6,974,479 B2 | 12/2005 | Trieu | |
| 7,445,634 B2 | 11/2008 | Trieu | |
| 7,455,685 B2 * | 11/2008 | Justis | 606/246 |
| 2006/0047341 A1 | 3/2006 | Trieu | |
| 2006/0085002 A1 | 4/2006 | Trieu et al. | |
| 2006/0095134 A1 | 5/2006 | Trieu et al. | |
| 2006/0106382 A1 | 5/2006 | Gournay et al. | |
| 2006/0161154 A1 | 7/2006 | McAfee | |
| 2007/0021801 A1 | 1/2007 | Heruth et al. | |
| 2007/0142842 A1 | 6/2007 | Krueger et al. | |
| 2007/0213660 A1 | 9/2007 | Richards et al. | |
| 2007/0265621 A1 | 11/2007 | Mathis et al. | |
| 2008/0009861 A1 | 1/2008 | Stark | |
| 2008/0021463 A1 | 1/2008 | Georgy | |
| 2008/0039843 A1 | 2/2008 | Abdou | |
| 2008/0154306 A1 | 6/2008 | Heinz | |
| 2009/0024174 A1 | 1/2009 | Stark | |
| 2009/0076517 A1 | 3/2009 | Reiley et al. | |
| 2009/0093817 A1 | 4/2009 | Zucherman et al. | |
| 2009/0099610 A1 | 4/2009 | Johnson et al. | |
| 2009/0149860 A1 | 6/2009 | Scribner et al. | |
| 2009/0181892 A1 | 7/2009 | Thorne et al. | |
| 2009/0216238 A1 | 8/2009 | Stark | |
| 2009/0263321 A1 | 10/2009 | McDonald et al. | |
| 2009/0263459 A1 | 10/2009 | King | |
| 2009/0264489 A1 | 10/2009 | Hidebrand et al. | |
| 2009/0264490 A1 | 10/2009 | Zanella et al. | |
| 2009/0264491 A1 | 10/2009 | McKay et al. | |

* cited by examiner

*Primary Examiner* — Eduardo C Robert
*Assistant Examiner* — Christina Negrelli

(57) ABSTRACT

A sacro-iliac implant delivery instrument includes a first arm connected to a first cannula. The first cannula is rotatable relative to the first arm and is configured for support of a fastening element. A second arm is connected to the first arm. The second arm is rotatable relative to the first arm and is configured for detachable connection to a sacro-iliac implant. The second arm and the first cannula are configured for rotation relative to the first arm to a preset orientation such that the second arm is disposed along a first predetermined trajectory for delivering the sacro-iliac implant and the first cannula is disposed along a second predetermined trajectory for delivering the fastening element in alignment with the sacro-iliac implant for transarticular fixation. Methods of use are disclosed.

18 Claims, 8 Drawing Sheets

SACRO-ILIAC JOINT IMPLANT SYSTEM, METHOD AND INSTRUMENT

TECHNICAL FIELD

The present disclosure generally relates to medical devices for the treatment of musculoskeletal disorders, and more particularly to an implant system and method for treating the sacro-iliac joint.

BACKGROUND

The sacroiliac (SI) joint is a diarthrodial joint that joins the sacrum to the ilium bones of the pelvis. In the SI joint, the sacral surface has hyaline cartilage that moves against fibrocartilage of the iliac surface. The spinal column is configured so that the weight of an upper body rests on the SI joints at the juncture of the sacrum and ilia. Stress placed on the SI joints in an upright position of the body makes the lower back susceptible to injury.

Disorders of the SI joint can cause low back and radiating buttock and leg pain in patients suffering from degeneration and laxity of the SI joint. In some cases, the SI joint can undergo dehydration and destabilization, similar to other cartilaginous joints, which causes significant pain. The SI joint is also susceptible to trauma and degeneration, from fracture and instability. It is estimated that disorders of the SI joint are a source of pain for millions of people suffering from back and radicular symptoms.

Non-surgical treatments, such as medication, injection, mobilization, rehabilitation and exercise can be effective, however, may fail to relieve the symptoms associated with these disorders. Surgical treatment of these disorders includes stabilization and/or arthrodesis. Stabilization can include the use of bone screws that are directly threaded into bone. Arthrodesis may include immobilization of a joint. The present disclosure describes an improvement over these prior art technologies.

SUMMARY OF THE INVENTION

Accordingly, an implant system and method is provided for treating the SI joint. It is contemplated that the system may include an implant configured for disposal with the SI joint. It is further contemplated that the implant system and method may be employed for an arthrodesis treatment.

In one particular embodiment, in accordance with the principles of the present disclosure, a sacro-iliac implant delivery instrument is provided. The sacro-iliac implant delivery instrument includes a first arm having a first end portion connected to a first cannula at a first pivot. The first cannula is rotatable about the first pivot relative to the first arm and is configured for support of a fastening element. A second arm is connected to the first arm at a second pivot. The second arm is rotatable about the second pivot relative to the first arm and is configured for detachable connection to a sacro-iliac implant. The second arm and the first cannula are configured for rotation relative to the first arm to a preset orientation such that the second arm is disposed along a first predetermined trajectory for delivering the sacro-iliac implant and the first cannula is disposed along a second predetermined trajectory for delivering the fastening element in alignment with the sacro-iliac implant for transarticular fixation.

In one embodiment, a sacro-iliac implant system is provided. The sacro-iliac implant system includes a first sacro-iliac implant defining at least one opening. At least one fastening element is configured for disposal in the at least one opening. A first sacro-iliac implant delivery instrument is provided, similar to those disclosed herein.

In one embodiment, a method for treating a sacro-iliac joint is disclosed. The method includes the steps of: providing a first sacro-iliac implant defining at least one opening; providing at least one fastening element; providing a first sacro-iliac implant delivery instrument, similar to those disclosed herein; preselecting a target location within the sacro-iliac joint for disposal of the first sacro-iliac implant; configuring the first sacro-iliac delivery instrument in a preset orientation such that the second arm is disposed along a first predetermined trajectory for delivering the first sacro-iliac implant and the first cannula is disposed along a second predetermined trajectory for delivering the fastening element in alignment with the sacro-iliac implant for transarticular fixation; delivering the first sacro-iliac implant within the sacro-iliac joint with the second arm disposed in the preset orientation; delivering the at least one fastening element within the sacro-iliac joint with the first cannula disposed in the preset orientation; inserting the at least one fastening element within the at least one opening of the first sacro-iliac implant; and securing the at least one fastening element in the transarticular fixation.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION OF THE INVENTION

Figure 1:
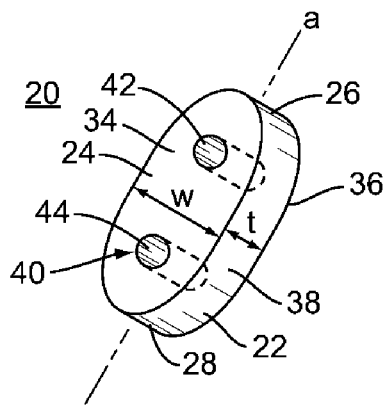
FIG. 1 is a perspective view of one particular embodiment of an implant of an implant system in accordance with the principles of the present disclosure.

The exemplary embodiments of the implant system and methods of use disclosed are discussed in terms of medical devices for the treatment of musculoskeletal disorders and more particularly, in terms of an implant system and method for treating the SI joint. It is envisioned that the implant system and methods of use disclosed provide stability and maintains structural integrity while reducing stress on the SI joint. It is further envisioned that the present disclosure may be employed to treat musculoskeletal disorders including sacro-Iliac dysfunction or syndrome, dehydration, destabilization, laxity, fracture, tumor, spinal disorders and other orthopedic disorders. It is contemplated that the present disclosure may be employed with surgical treatments, including open surgery, percutaneous and minimally invasive procedures of such disorders, such as, for example, arthrodesis including fusion, bone graft and implantable prosthetics. It is further contemplated that the present disclosure may be employed with other osteal and bone related applications, including those associated with diagnostics and therapeutics. The disclosed implant system and methods may be employed in a surgical treatment with a patient in a prone or supine position, employing a posterior, lateral, inferior, posterior-inferior, superior or anterior approach. The present disclosure may be employed with procedures for treating the lumbar, cervical, thoracic and pelvic regions of a spinal column.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

The following discussion includes a description of an implant system, related components and exemplary methods of employing the implant system in accordance with the principles of the present disclosure. Alternate embodiments are also disclosed. Reference will now be made in detail to the exemplary embodiments of the present disclosure, which are illustrated in the accompanying figures. Turning now to FIGS. 1-4, there are illustrated components of the implant system in accordance with the principles of the present disclosure.

The components of the implant system are fabricated from materials suitable for medical applications, including metals, synthetic polymers, ceramics, bone, biocompatible materials and/or their composites, depending on the particular application and/or preference of a medical practitioner. For example, components of the implant system, such as, for example, an implant body, an outer surface of the implant body and/or portions thereof, cavities of the implant body, which may be monolithically formed, integrally connected or configured as an insert with the body, fastening elements and/or instruments, discussed below, can be fabricated from materials such as commercially pure titanium, titanium alloys, Grade 5 titanium, super-elastic titanium alloys, cobalt-chrome alloys, stainless steel alloys, superelastic metallic alloys (e.g. Nitinol, super elasto-plastic metals, such as GUM METAL® manufactured by Toyotsu Material Incorporated of Japan), thermoplastics such as polyaryletherketone (PAEK) including polyetheretherketone (PEEK), polyetherketoneketone (PEKK) and polyetherketone (PEK), carbon fiber reinforced PEEK composites, PEEK-BaSO$_4$ composites, ceramics and composites thereof such as calcium phosphate (e.g. SKELITE™ manufactured by Biologix Inc.), rigid polymers including polyphenylene, polyamide, polyimide, polyetherimide, polyethylene, polyurethanes of any durometer, epoxy, silicone, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Different components of the implant system may have alternative material composites to achieve various desired characteristics such as strength, rigidity, elasticity, compliance, biomechanical performance, durability and radiolucency or imaging preference. The components of the implant system may also be fabricated from a heterogeneous material such as a combination of two or more of the above-described materials.

It is envisioned that the components of the implant system can be manufactured via various methods. For example, the implant body can be manufactured and assembled via injection-molding, insert-molding, overmolding, compression molding, transfer molding, co-extrusion, pultrusion, dip-coating, spray-coating, powder-coating, porous-coating, milling from a solid stock material, and their combinations. One skilled in the art, however, will realize that such materials and fabrication methods suitable for assembly and manufacture, in accordance with the present disclosure, would be appropriate.

The implant system includes an orthopedic implant, such as, for example, a sacro-iliac implant 20, which is configured, for example, to treat S-I joint disorders including those caused by degeneration or trauma. It is contemplated that sacro-iliac implant 20 may be employed for arthrodesis applications, as will be described.

Sacro-iliac implant 20 includes a body 22 that is elongated along a longitudinal axis α thereof. Body 22 has an elliptical configuration and defines an outer surface 24. Outer surface 24 is configured to engage and space apart opposing articular surfaces A of a sacro-iliac joint J. It is contemplated that articular surface A may refer to a sacral surface $S_1$ of a sacrum S and/or an iliac surface $I_1$ of an ilium I. Body 22 is configured to engage opposing articular surfaces such as sacral surface $S_1$ and iliac surface $I_1$ and/or opposing valleys or peaks of an individual sacrum S or ilium I. Body 22 may have a solid, hollow, porous or cage configuration. Outer surface 24 has a continuously even or smooth configuration. It is contemplated that outer surface 24 is configured to substantially match articular surface(s) A and/or may be substantially smooth, rough, textured, spiked, semi-porous, dimpled and/or polished.

Body 22 extends from a first end 26 to a second end 28. Body 22 has a thickness t and a width w, according to the requirements of the particular application. It is envisioned that thickness t may be in a range of approximately 1-12 millimeters (mm), and preferably in a range of approximately 3 to 9 mm. It is contemplated that width w may be in a range of approximately 5-30 mm, and preferably in a range of approximately 10-25 mm. This configuration of body 22 facilitates disposal and fixation of body 22 within an SI joint, such that, for example, body 22 separates articular surfaces A to dilate the SI joint and prevent joint surfaces from undesired engagement such as that caused by degeneration and cartilage wear. It is contemplated that such spacing apart of the articular surfaces of the SI joint tensions ligaments, supports the SI joint and provides maximum stabilization of the SI joint. It is further contemplated that the overall and/or cross-sectional geometry of body 22 may have various configurations, for example, round, oval, oblong, triangular, rectangular, polygonal, irregular, uniform, non-uniform, consistent or variable.

Body 22 has a first side surface 34 and an opposing second side surface 36 that extend along width w. Outer surface 24 includes adjacent edge surfaces 38 disposed about the perimeter of body 22, and extending between first side surface 34 and second side surface 36, along thickness t. It is envisioned that thickness t may be unequal along surface 34, 36 such that surface 34, 36 may be offset, tapered, converging and/or diverging.

It is envisioned that body 22 can be variously configured and dimensioned with regard to size, shape, thickness, geometry and material. Body 22 may also be formed of one or a plurality of elements such as spaced apart portions, staggered patterns and mesh. It is envisioned that the particular geometry and material parameters of body 22 may be selected to modulate the flexibility or stiffness of sacro-iliac implant 20, such as those examples discussed herein. For example, body 22 can be configured to have varying ranges or degrees of flexibility or stiffness such as rigid, compliant, or reinforced. Depending on the flexibility or stiffness of body 22, the flexibility or stiffness of sacro-iliac implant 20 can be contoured according to the requirements of a particular application. It is contemplated that the ability to vary stiffness of sacro-iliac implant 20 promotes fusion of the elements of sacro-iliac joint J. It is envisioned that the components of sacro-iliac implant 20 may be monolithically formed, integrally connected or arranged with attaching elements.

Body 22 defines a plurality of cavities, such as, for example, openings 40 extending through body 22. Openings 40 include a first opening 42 disposed adjacent first end 26 and a second opening 44 disposed adjacent second end 28. Openings 42, 44 are disposed with body 22 in an orientation facing articular surfaces A, sacral surface $S_1$ and iliac surface $I_1$. It is envisioned that body 22 may include one or a plurality of openings 40. It is further envisioned that the cavities may include through holes, slots, voids, indentations, and/or non-interference configurations and dimensions.

The implant system includes a plurality of fastening elements, such as, for example, screws 46 that are delivered to sacro-iliac joint J to pass through the joint surfaces. Screws 46 are transarticular and configured for fixation with the articular surfaces A, sacral surface $S_1$ and iliac surface $I_1$, to secure body 22 with sacro-iliac joint J for stabilization and immobilization thereof. Screws 46 include a first screw 48 (FIG. 3) configured for disposal in opening 42 and a second screw 50 configured for disposal in the opening 44. It is envisioned that screws 48, 50 include threaded portions to facilitate securement with joint surfaces of sacro-iliac's joint J. It is further envisioned that the fastening elements may alternatively include anchors and/or bolts, and may be secured via interference/friction fit, clips and/or nuts. It is contemplated one or a plurality of fastening elements may be employed.

In one embodiment, one or a plurality of openings 40 may be configured to expel and/or elute at least one agent therefrom. Such an opening(s) 40 may includes one or a plurality of agent reservoirs. The agent reservoirs can be configured as drug depots with medication for pain and may include antibiotics and/or therapeutics. Diffusion of such agents can occur through openings 40. It is envisioned that body 22 includes a network of agent diffusing openings 40 (not shown) interconnected and/or in fluid communication. It is contemplated that body 22 and/or each of openings 40 may include one or a plurality of agents. Openings 40 may be oriented parallel to articular surfaces of a SI joint, perpendicular, randomly oriented, and/or configured for multiple directional expulsion or eluting.

It is envisioned that the agent reservoirs contains active agents and may include one or a plurality of therapeutic agents and/or pharmacological agents for release, including sustained release, into SI joint J to treat, for example, pain, inflammation and degeneration. The agents may include pharmacological agents, such as, for example, antibiotics, pain medications, analgesics, anesthetics, anti-inflammatory drugs including but not limited to steroids, anti-viral and anti-retroviral compounds, therapeutic proteins or peptides, therapeutic nucleic acids (as naked plasmid or a component of an integrating or non-integrating gene therapy vector system), and combinations thereof.

The agent may also include analgesics or anesthetics such as acetic acid derivatives, clonidine, COX-2 selective inhibitors, COX-2 inhibitors, enolic acid derivatives, propionic acid derivatives, salicylic acid derivatives, opioids, opioid/nonopioid combination products, adjuvant analgesics, and general and regional/local anesthetics.

The agent may also include antibiotics such as, for example, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole, and vancomycin.

The agent may also include immunosuppressives agents, such as, for example, steroids, cyclosporine, cyclosporine analogs, cyclophosphamide, methylprednisone, prednisone, azathioprine, FK-506, 15-deoxyspergualin, prednisolone, methotrexate, thalidomide, methoxsalen, rapamycin, leflunomide, mizoribine (Bredinin™), brequinar, deoxyspergualin, and azaspirane (SKF 105685), Orthoclone OKT™ 3 (muromonab-CD3). Sandimmune™, Neoral™, Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen) and Rapamuen™ (sirolimus).

It is envisioned that openings 40 are capable of accepting at least one agent before, during and/or after implantation with joint J, holding the at least one agent in a reservoir, and/or delivery in vivo of the at least one agent to tissues of joint J and tissues surrounding joint J, including bone. Openings may be replenished, via one or a plurality of iterations, with therapeutic and/or pharmacological agents.

The at least one agent may be eluted from openings 40 via an unstressed, free-flowing fluid communication with joint tissues, including bone, engaging outer surface 24. The at least one agent may also be expelled via compression of body 22 between articular surfaces A. The at least one agent may also permeate or diffuse the at least one agent through the material of body 22.

In one embodiment, the implant system includes a plurality of bodies 22, described above. It is contemplated that employing the plurality of bodies 22 can optimize the amount sacro-iliac joint J can be spaced apart such that a joint space dimension can be preselected. The plurality of bodies 22 can be inserted through the same or an alternate trajectory. The plurality of bodies 22 can be oriented in a side by side engagement, spaced apart and/or staggered. It is envisioned that one or all of the plurality of bodies 22 may be inserted via a trajectory oriented from an anterior, posterior, superior or inferior direction, similar to that described herein. It is further envisioned that one or a plurality of bodies 22 may be used.

Figure 2:
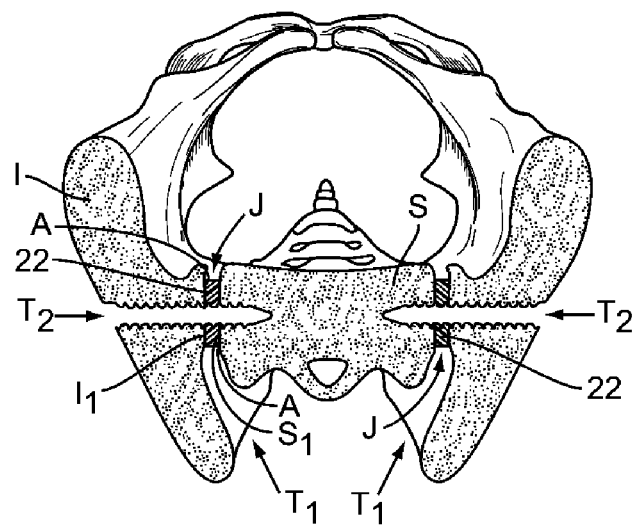
FIG. 2 is a plan view, in part cross section, of a sacro-iliac/ilio-pelvic region.
Figure 3:
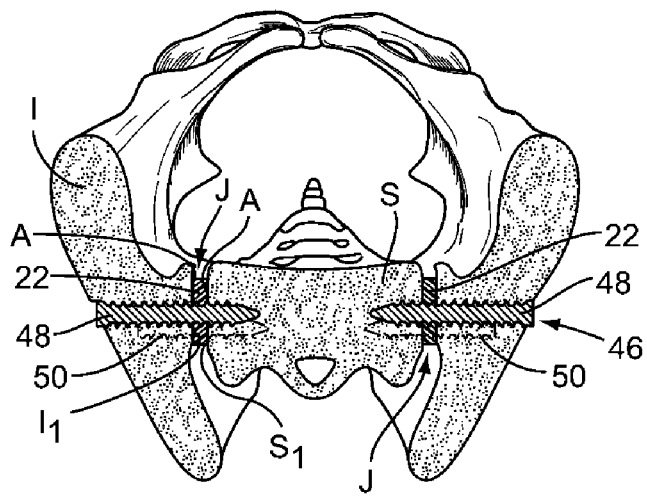
FIG. 3 is a plan view, in part cross section, of an implant system including the implant shown in FIG. 1 and the region shown in FIG. 2.
Figure 4:
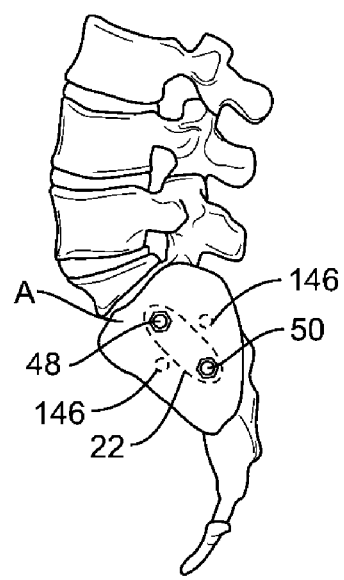
FIG. 4 is a side view of the implant system, partially shown in phantom, and the region shown in FIG. 3.

In assembly, operation and use, the implant system including sacro-iliac implant 20 is employed with a surgical procedure for treatment of a sacro-iliac joint J of a patient, as discussed herein. The implant system may also be employed with other surgical procedures. In particular, the implant system is employed with a surgical arthrodesis procedure, such as, for example, fusion for treatment of an applicable condition or injury of an affected sacro-iliac joint J, as shown in FIGS. 2-4. It is contemplated that the implant system is inserted with sacro-iliac joint J to space apart articular joint surfaces, establish joint tension, provide support and maximize stabilization of sacro-iliac joint J. It is further contemplated that the implant system is inserted with a sacro-iliac joint J as a SI joint spacer to restore ligamentous tension, eliminate painful micro-motion, and/or separate and cushion opposing articulating surfaces that cause pain. It is envisioned that the implant system may maintain joint tension without promoting bone growth.

In use, to treat the affected section of sacro-iliac joint J, a medical practitioner obtains access to a surgical site including sacro-iliac joint J in any appropriate manner, such as through incision and retraction of tissues. It is envisioned that the implant system may be used in any existing surgical method or technique including open surgery, mini-open surgery, minimally invasive surgery and percutaneous surgical implantation, whereby sacro-iliac joint J is accessed through a mini-incision, or sleeve that provides a protected passageway to the area. Once access to the surgical site is obtained, the particular surgical procedure is performed for treating the sacro-iliac joint disorder. The implant system is then employed to augment the surgical treatment. The implant system can be delivered or implanted as a pre-assembled device or can be assembled in situ. The implant system may be completely or partially revised, removed or replaced in situ. It is contemplated that one or all of the components of the implant system can be delivered to the surgical site via manual manipulation and/or a free hand technique.

A first trajectory $T_1$, as shown in FIG. 2, is defined for insertion and/or injection of body 22 of sacro-iliac implant 20 within sacro-iliac joint J. Implant 20 is inserted via the protected passageway along the defined trajectory $T_1$ into sacro-iliac joint J. A cavity of sacro-iliac joint J is prepared along trajectory $T_1$ for disposal of sacro-iliac implant 20.

The protected passageway includes a dilator/delivery tube (not shown) configured to deliver sacro-iliac implant 20 directly to the joint space of sacro-iliac joint J. It is envisioned that the dilator/delivery tube may be configured as an in-situ guidable instrument, and may include an endoscope camera tip for viewing insertion trajectory. It is further envisioned that body 22 may include a cavity configured to receive the instrument to facilitate delivery of sacro-iliac implant 20 to sacro-iliac joint J. It is contemplated that body 22 and/or other components of the implant system, and the several embodiments of the implant system and body described herein, may include a connecting portion, opening and/or mechanism, such as, for example, threaded holes, snap-on connects, and quick-connect mechanisms for connection to a delivery instrument for implant disposal, detachable connection and release and removal from the surgical site.

Sacro-iliac implant 20 is manipulated such that side surfaces 34, 36 of body 22 engage opposing articular surfaces A, according to the contour of articular surfaces A. Manipulation can include pushing, pulling, rotation of sacro-iliac implant 20, rotation of sacro-iliac implant 20 about the joint axis once implanted and/or by mechanical devices. It is contemplated that body 22 may engage only one or a plurality of articular surfaces A. It is further contemplated that openings 42, 44 and/or side surfaces 34, 36 can be oriented for a preset, predetermined and/or guided to a predetermined orientation for disposal with articular surfaces A. For example, openings 42, 44 can have a preset orientation such that the fastening elements can be secured with the surfaces of sacro-iliac joint J at predetermined locations.

Sacro-iliac implant 20 is disposed with sacro-iliac joint J for treating the sacro-iliac joint disorder. Body 22 is configured for compliant engagement with articular surfaces A. Opposing side surfaces 34, 36 engage and space apart respective opposing articular surfaces, sacral surface $S_1$ and iliac surface $I_1$, and is secured within joint J to stabilize and immobilize portions of sacrum S and ilium I of sacro-iliac joint J.

Upon placement of body 22, body cavities are tapped and/or drilled in the joint surfaces of sacro-iliac joint J in an orientation and alignment with openings 42, 44 of body 22. It is contemplated that a guide instrument, examples of which being discussed below, may be used to facilitate formation of such cavities by providing an alignment device for a surgical drill and/or tap. Screw 48 is delivered via the guide instrument to the sacro-iliac joint J into alignment with opening 42 along a second trajectory $T_2$. Screw 50 is similarly delivered via the guide instrument to the sacro-iliac joint J into alignment with opening 44 along second trajectory $T_2$. Screws 48, 50 are threaded with the joint surfaces of sacro-iliac joint J and/or body 22 for fixation therewith to secure, stabilize and immobilize sacro-iliac joint J. This configuration tensions the joint ligaments of sacro-iliac joint J. This configuration also spaces and supports sacro-iliac joint J to stabilize and treat a sacro-iliac disorder. It is envisioned that trajectory $T_1$ may be oriented perpendicular, parallel, angularly offset, offset, cruciate and/or staggered relative to trajectory $T_2$. The guide instrument releases screws 48, 50 and is removed from the surgical site.

In one embodiment, as shown in FIG. 4, the implant system includes fastening elements, such as, for example, screws 146 configured for fixation with articular surfaces A external to body 22. Screws 146 are employed to secure joint surfaces and provide complementary stabilization and immobilization to sacro-iliac joint J. Sacro-iliac implant 20 may include locking structure to facilitate fixation of implant 20 within the joint space of sacro-iliac joint J, examples of which being discussed below.

It is contemplated that the implant system including sacro-iliac implant 20 may be employed during a surgical fusion procedure for treatment of a condition or injury, such as, degeneration or fracture. Fixation of sacro-iliac implant 20 with articular surfaces A and/or other portions of sacro-iliac joint J can be facilitated by the resistance provided by the joint space and/or engagement with the outer articular structures.

Sacro-iliac implant 20 may include locking structure to facilitate fixation with articular surface(s) A. It is envisioned that such locking structure may include fastening elements such as, for example, clips, hooks, adhesives and/or flanges, as will be described below. It is further envisioned that in joint fusion applications of sacro-iliac implant 20, body 22 includes voids, cavities and/or openings for including therapeutic polynucleotides or polypeptides and bone growth promoting material, such as those described herein, which can be packed or otherwise disposed therein.

For example, outer surface 24 and/or openings 40 may include at least one agent including biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, biologically active agents coated onto the exterior of implant 20 and/or applied thereto for gradual release such as by blending in a bioresorbable polymer that releases the biologically active agent or agents in an appropriate time dependent fashion as the polymer degrades within the patient. Suitable biologically active agents include, for example, bone morphogenic protein (BMP) and cytokines.

It is contemplated that the implant system including body 22, outer surface 24, opening(s) 40 and/or large cavities and slots of body 22, and any fastening elements, and attachments may be coated, formed of, and/or impregnated with an osteoconductive and/or osteoinductive material such as HA and/or osteoinductive agent and/or bone growth factors such as BMP, either partially or completely to enhance osteointegration and fusion across the joint, and/or for enhanced bony fixation to the treated area. It is contemplated that such materials may include a combination of materials such as, for example, an HA coating with BMP for improved fusion rate. It is further contemplated that such materials may include pharmacological agents as described herein. It is envisioned that the components of body 22 may include large cavities or slots configured to receive fasteners and/or pack bone graft, such as, for example, autograft, allograft, bone chips, demineralized bone matrix, calcium phosphate, HA, and bone growth agents in a carrier matrix for enhancing fusion.

Sacro-iliac implant 20 can be made of radiolucent materials such as polymers. Radiomarkers may be included for identification under x-ray, fluoroscopy, CT or other imaging techniques.

Figure 5A:
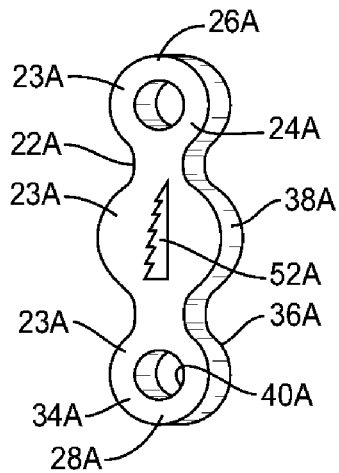
FIG. 5A-X are perspective views of embodiments of the implant shown in FIG. 1.
Figure 5B:
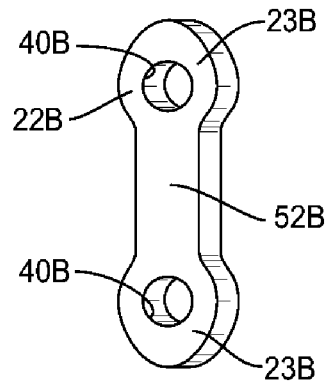
Figure 5C:
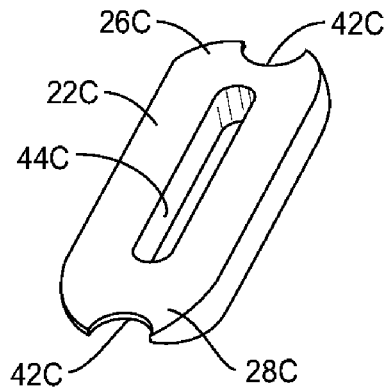
Figure 5D:
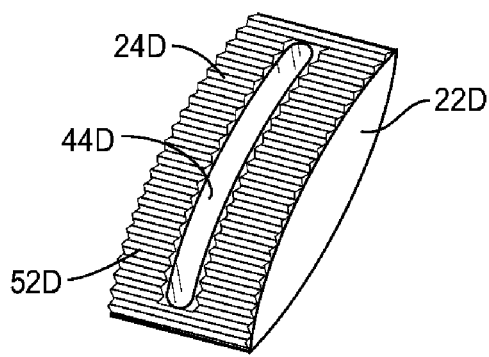
Figure 5E:
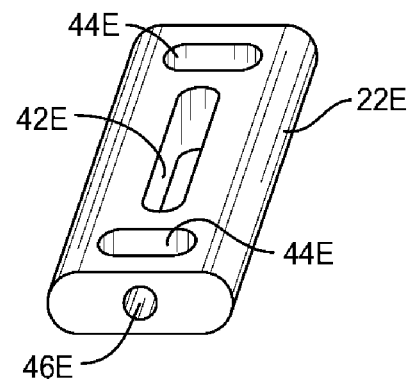
Figure 5F:
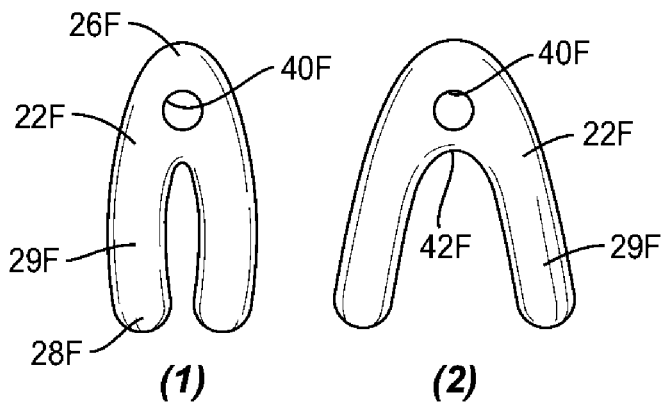
Figure 5G:
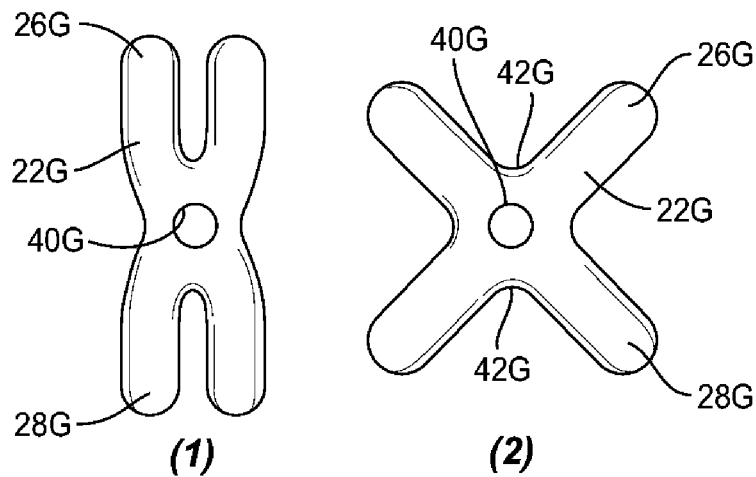
Figure 5H:
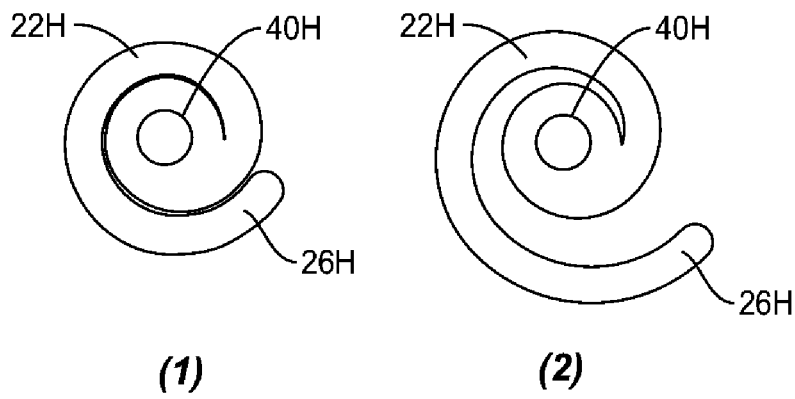
Figure 5I:
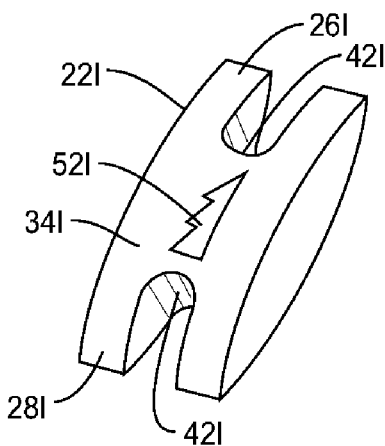
Figure 5J:
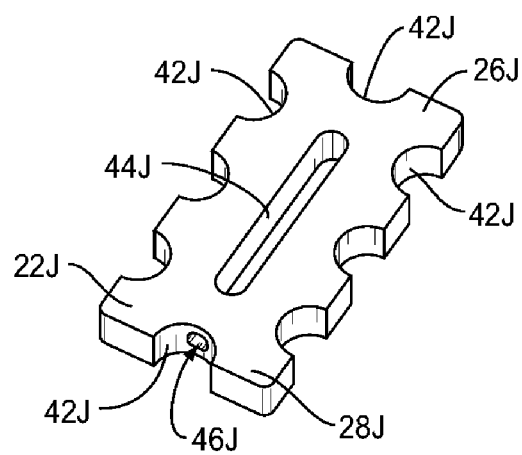
Figure 5K:
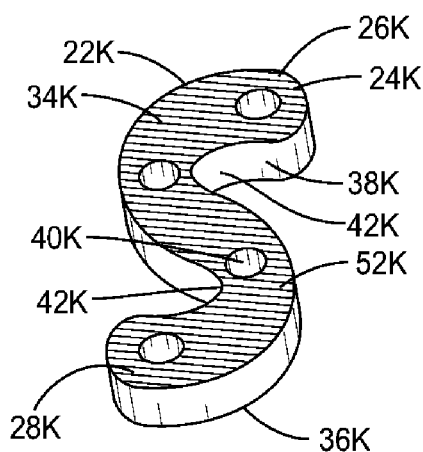
Figure 5L:
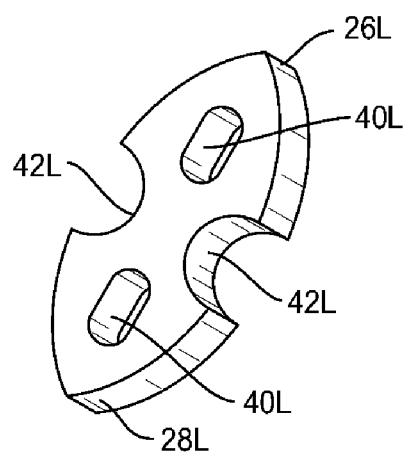
Figure 5M:
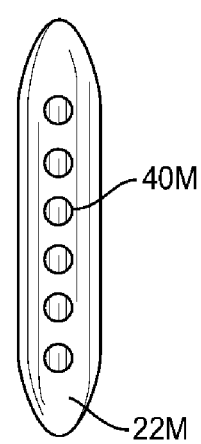
Figure 5N:
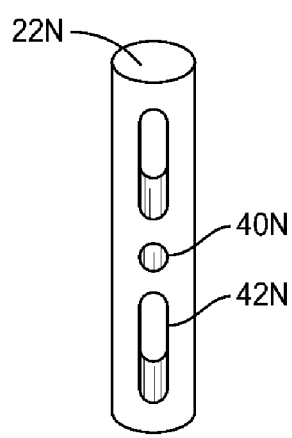
Figure 5O:
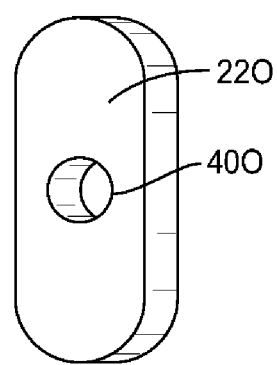
Figure 5P:
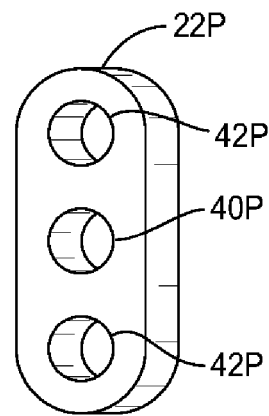
Figure 5Q:
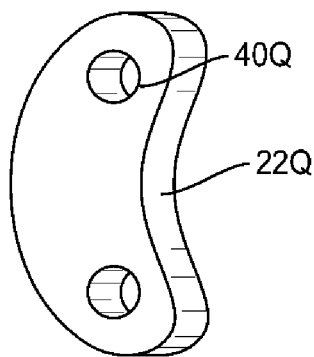
Figure 5R:
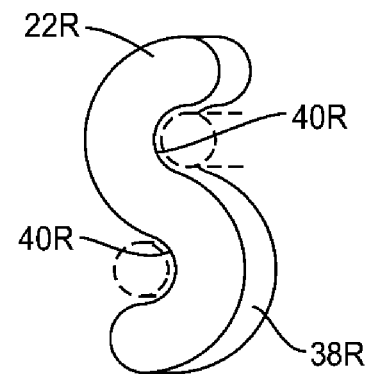
Figure 5S:
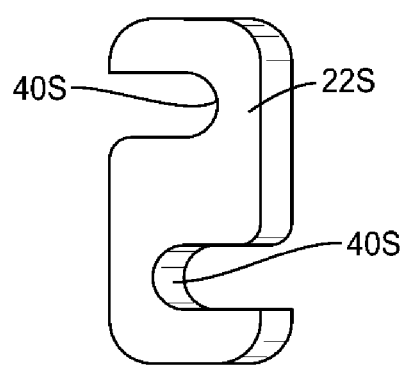
Figure 5T:
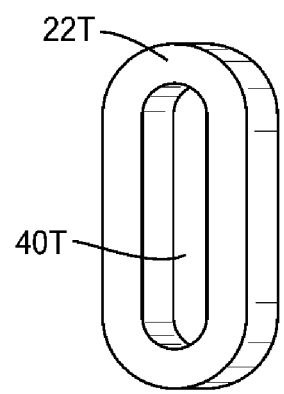
Figure 5U:
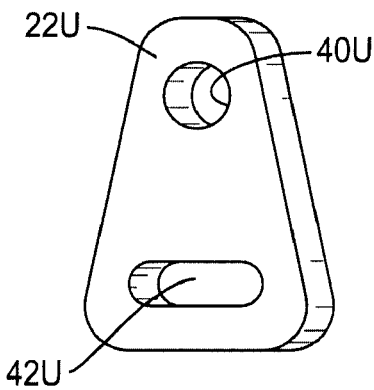
Figure 5V:
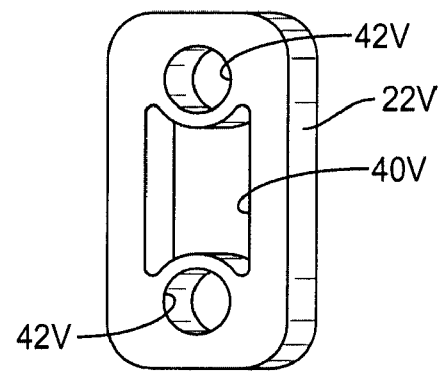
Figure 5W:
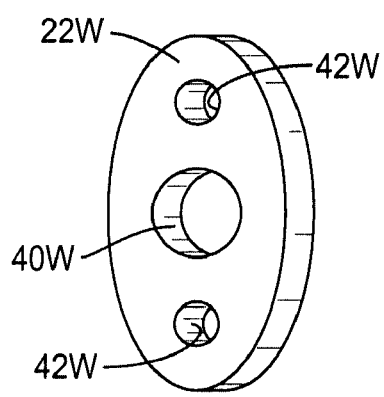
Figure 5X:
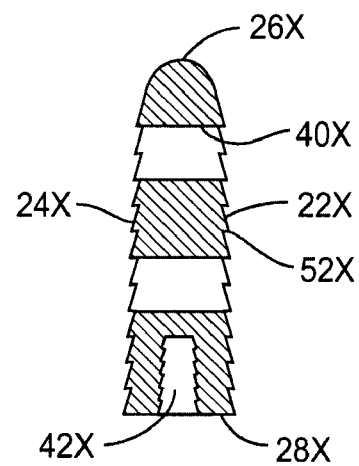

Referring to FIGS. 5A-X, embodiments of sacro-iliac implant 20 are shown. In one embodiment, as shown in FIG. 5A, sacro-iliac implant 20 includes a body 22A, similar to body 22 described above. Body 22A has an elongated, link configuration including connected links 23A. Body 22A extends from a first end 26A to a second end 28A. Body 22A has an outer surface 24A, which includes planar surfaces 34A, 36A, and an undulating side surface 38A. End links 23A each include an opening 40A, similar to opening 40 described above. Surface 34A includes a locking element, such as, for example, a keel 52A extending therealong. Keel 52A is serrated and configured for penetrating engagement with an articular surface of a SI joint to fix body 22A with the articular surface. FIG. 5B shows a body 22B having end links 23B, each having an opening 40B, and being connected by an extension 52B.

In one embodiment, as shown in FIG. 5C, sacro-iliac implant 20 includes an elongated body 22C, similar to body 22 described above. Body 22C extends from a first end 26C to a second end 28C. Body 22C includes openings, similar to openings 40 described above, which include grooves 42C disposed adjacent ends 26C, 28C, and an elongated slot 44C. FIG. 5D shows a body 22D having an opening including an elongated slot 44D, and an outer surface 24D including a locking element, such as, for example, serrations 52D extending therealong, which are configured for penetrating engagement with an articular surface of a SI joint to fix body 22D with the articular surface. FIG. 5E shows a body 22E having openings, which include a central slot 42E, transverse slots 44E and an opening 46E configured to receive a delivery and/or guide instrument.

In one embodiment, as shown in FIG. 5F, sacro-iliac implant 20 includes an elongated body 22F, similar to body 22 described above. Body 22F is formed of a superelastic metallic alloy, examples of which being described above. Body 22F extends from a first end 26F to a second end 28F. Second end 28F includes arms 29F extending from body 22F. Body 22F is initially disposed in an unstressed orientation (F2) with arms 29F flared outward. Body 22F is manipulated with an externally applied force such that arms 29F are compressed (F1) into a linear orientation profile for insertion through a reduced size opening in SI joint tissues. Body 22F is then delivered to a joint space via a protected passageway, similar to that described above. Upon delivery of body 22F to the joint space, arms 29F expand to engage articular surface(s) of a SI joint for disposal with the S-I joint due to the shape memory configuration, which is resistant to migration or expulsion. Body 22F has openings, which include an opening 40F and a groove 42F configured for receipt of a fastening element, similar to opening 40 described above.

FIG. 5G shows a body 22G formed of a superelastic metallic alloy and having first arms 26G and second arms 28G extending in opposing directions from body 22G. Body 22G is initially disposed in an unstressed orientation (G2) with arms 26G, 28G flared outward. Body 22F is manipulated with an externally applied force such that arms 26G, 28G are compressed (G1) into a linear orientation profile for insertion through a reduced size opening in SI joint tissues. Body 22G is then delivered to a joint space via a protected passageway, similar to that described above. Upon delivery of body 22G to the joint space, arms 26G, 28G expand to engage articular surface(s) of a SI joint for disposal within the S-J joint due to the shape memory configuration, which is resistant to migration or expulsion. Body 22G has openings, which include an opening 40G and grooves 42G configured for receipt of a fastening element, similar to opening 40 described above.

FIG. 5H shows a body 22H formed of a superelastic metallic alloy and having a coiled arm 26H extending from body 22H. Body 22H is initially disposed in an unstressed orientation (H2) with arm 26H flared outward. Body 22H is manipulated with an externally applied force such that arm 26H is compressed (H1) into a linear orientation. Body 22H is then delivered to a joint space via a protected passageway, similar to that described above. Upon delivery of body 22H to the joint space, arm 26H expands to engage articular surface (s) of a SI joint for disposal within the S-J joint due to the shape memory configuration. Body 22H has an opening 40H.

In one embodiment, as shown in FIG. 5I, sacro-iliac implant 20 includes an elongated body 22I, similar to body 22 described above. Body 22I extends from a first end 26I to a second end 28I. Body 22I includes openings, similar to openings 40 described above, which include grooves 42I disposed adjacent ends 26I, 28I. A surface 34I includes a locking element, such as, for example, a keel 52I extending therealong. Keel 52I is serrated and configured for
penetrating engagement with an articular surface of a SI joint to fix body 22I with the articular surface.

FIG. 5J shows an elongated body 22J extending from a first end 26J to a second end 28J. Body 22J includes openings, similar to openings 40 described above, which include grooves 42J disposed about the perimeter of body 22J, an elongated slot 44J and an opening 46J configured to receive a delivery and/or guide instrument.

In one embodiment, as shown in FIG. 5K, sacro-iliac implant 20 includes a body 22K, similar to body 22 described above. Body 22K has an elongated configuration and extends from a first end 26K to a second end 28K. Body 22K has an outer surface 24K, which includes surfaces 34K, 36K, and an undulating side surface 38K. Surfaces 34K, 36K include a locking element, such as, for example, serrations 52K extending therealong, which are configured for penetrating engagement with an articular surface of a SI joint to fix body 22K with the articular surface. Body 22K has openings, which include openings 40K and grooves 42K configured for receipt of a fastening element, similar to opening 40 described above.

In one embodiment, as shown in FIG. 5L, sacro-iliac implant 20 includes an elongated body 22L extending from a first pointed end 26L to a second pointed end 28L. Body 22L has openings, which include oval slots 40L and grooves 42L, similar to opening 40 described above. It is contemplated that ends 26L, 28L may include an attachment for connection to a delivery and/or guide instrument.

FIG. 5M shows an elongated body 22M having an oval configuration and including a plurality of openings 40M. FIG. 5N shows an elongated cylindrical body 22N. Body 22N has openings, which include a central opening 40N and slots 42N. FIG. 5O shows an elongated body 22O including a single central opening 40O. FIG. 5P shows an elongated body 22P having a plurality of openings, which include a central opening 40P and end openings 42P. FIG. 5Q shows an elongated arcuate body 22Q having a plurality of openings, which include end openings 40Q. FIG. 5R shows an elongated body 22R having undulating side surfaces 38R and a plurality of openings, which include grooves 40R, similar to openings 40 described above. FIG. 5S shows an elongated body 22S having a plurality of openings, which include opposing grooves 40S, similar to openings 40 described above.

FIG. 5T shows an elongated elliptical body 22T defining an elongated elliptical slot 40T. FIG. 5U shows a body 22U having a triangular configuration and including a plurality of openings, which include an opening 40U and a transverse slot 42U. FIG. 5V shows an elongated body 22V having a plurality of openings, which include a central enlarged, rectangular opening 40V and end openings 42V, similar to openings 40 described above. FIG. 5W shows an elongated body 22W having a plurality of openings, which include a central enlarged, circular opening 40W and end openings 42W, similar to openings 40 described above.

In one embodiment, as shown in FIG. 5X in cross section, sacro-iliac implant 20 includes an elongated cylindrical body 22X extending from an arcuate end surface 26X to a planar end surface 28X. Body 22X has a plurality of openings, which include openings 40X and an opening 42X configured for receipt of a delivery and/or guide instrument. Body 22X has a circumferential outer surface 24X including a locking element, such as, for example, serrations 52X extending therealong, which are configured for penetrating engagement with an articular surface of an SI joint to fix body 22X with the articular surface.

Figure 6:
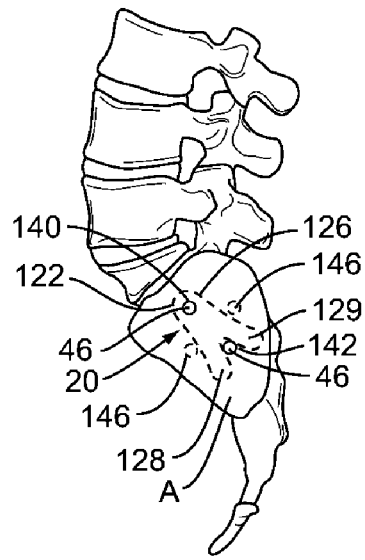
FIG. 6 is a side view of one embodiment of the implant system, partially shown in phantom, and the region shown in FIG. 4.

In one embodiment, as shown in FIG. 6, sacro-iliac implant 20 includes an elongated body 122, similar to body 22 described above. Body 122 extends from a first end 126 to a second end 128. Second end 128 includes arms 129 extending from body 122. Body 122 has a plurality of openings, similar to openings 40 described above, which include an opening 140 and a groove 142 defined by arms 129. The implant system includes fastening elements, such as, for example, screws 46 and screws 146, described above, configured for fixation with articular surfaces A. Screws 46 extend through opening 140 and groove 142. Screws 146 are configured for fixation with articular surfaces A external to body 122. Screws 46, 146 are employed to secure the components of sacro-iliac implant 20 and the joint surfaces of sacro-iliac joint J to provide complementary stabilization and immobilization to sacro-iliac joint J.

Figure 7:
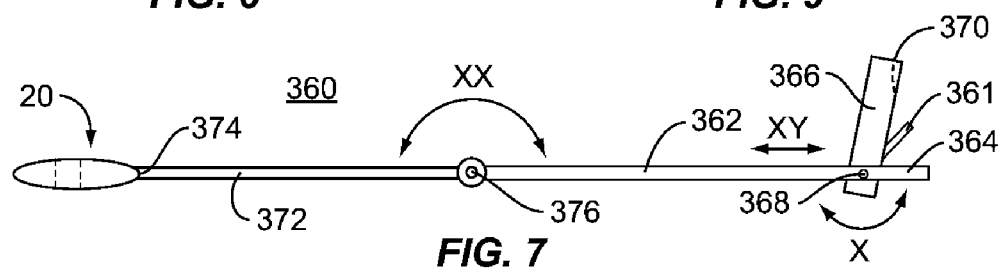
FIG. 7 is a side view of one embodiment of an instrument of the implant system in accordance with the principles of the present disclosure.
Figure 8:
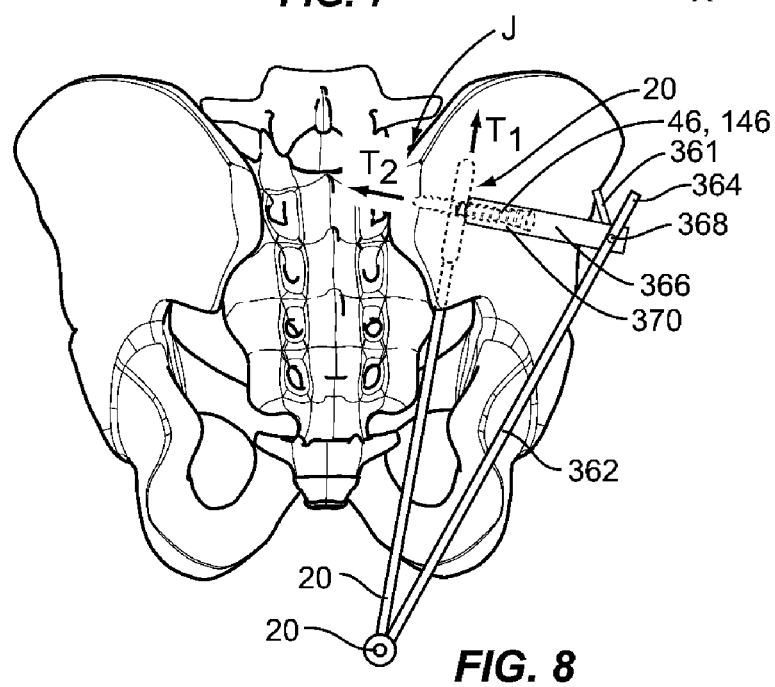
FIG. 8 is a plan view of the one embodiment of the implant system including the instrument shown in FIG. 7 and a sacro-iliac/ilio-pelvic region.

Referring to FIGS. 7 and 8, in one embodiment similar to the assembly, operation and use described with regard to FIGS. 1-4, the implant system including sacro-iliac implant 20 is employed with a surgical arthrodesis procedure for treatment of a sacro-iliac joint J of a patient using a targeting delivery instrument 360. Instrument 360 includes a first arm, such as, for example, an elongated, cannula arm 362 having an end 364 configured for connection to a cannula 366. Cannula 366 is movably connected to cannula arm 362 at a pivot point 368. Cannula 366 is rotatable about pivot point 368 through an angle of 360 degrees, in a clockwise or a counter clockwise direction as shown by arrows X, relative to cannula arm 362. Cannula 366 and cannula pivot point 376 are movable, in the direction shown by arrows XY, within a slot (not shown) of cannula arm 362 to facilitate slidable translation of cannula 366 relative to cannula arm 362. Cannula 366 is configured for rotation and translation to a predetermined orientation corresponding to a preselected trajectory for securing a fastening element with the components of the implant system and/or SI joint tissues, including bone. Instrument 360 includes a position lock, such as, for example, a cannula lock 361 connected to cannula arm 362 adjacent end 364 to lock cannula 366 in a predetermined orientation. It is contemplated that cannula 366 may be locked in any orientation through the angle of 360 degrees about pivot point 368. Cannula 366 has a passageway 370 and is configured to receive and support a fastening element, such as, for example, screws 46, 146. Cannula 366 facilitates delivery of screws 46, 146 to the SI joint, as will be described. It is envisioned that one or a plurality of cannulas may be employed.

Instrument 360 includes a second arm, such as, for example, a swing arm 372 having an end 374 configured for detachable connection to an implant, such as, for example, implant 20. Swing arm 372 is movably connected to cannula arm 362 at a cannula pivot point 376. Swing arm 372 is rotatable about pivot point 376 through an angle of 360 degrees, in a clockwise or a counter clockwise direction as shown by arrows XX, relative to cannula arm 362. Swing arm 372 and cannula arm 362 are relatively rotatable such that implant 20 is rotatable to a predetermined orientation corresponding to a preselected trajectory for securing implant 20 between articular surfaces of a SI joint, and/or further facilitate orientation of cannula 366 to a predetermined orientation corresponding to a preselected trajectory for securing a fastening element with the components of the implant system and/or SI joint tissues, including bone, as will be described. It is envisioned that one or a plurality of swing arms may be employed for delivery of one or a plurality of implants.

In use, to treat the affected section of sacro-iliac joint J, a medical practitioner conducts an investigation of the SI joint site to determine a location for implant 20 and fixation of screws 46. The location for implant 20 and fixation of screws 46 are predetermined and targeted. The medical practitioner obtains access to a surgical site including sacro-iliac joint J in any appropriate manner, similar to that described herein. A first trajectory $T_1$, corresponding to the predetermined location of implant 20, is defined for insertion and/or injection of sacro-iliac implant 20 within sacro-iliac joint J. Swing arm 372, cannula arm 362 and cannula 366 are preset according to the predetermined target locations for implant 20 and screws 46. Implant 20 is connected to end 374 and implant 20 is inserted via the protected passageway, described above, along the defined trajectory $T_1$ into sacro-iliac joint J. A cavity of sacro-iliac joint J is prepared along trajectory $T_1$ for disposal of sacro-iliac implant 20. A guide wire, needle and/or trocar may be employed to penetrate tissues and create a pathway through the body of a patient to the SI joint site.

Sacro-iliac implant 20 is manipulated to engage opposing articular surfaces, described above, of the SI joint. Sacro-iliac implant 20 is disposed with sacro-iliac joint J for treating the sacro-iliac joint disorder in an orientation for engaging and spacing apart the respective opposing articular surfaces. Implant 20 is secured within joint J to stabilize and immobilize portions of the sacrum and ilium of sacro-iliac joint J.

Upon placement of sacro-iliac implant 20, cavities are tapped and/or drilled in the joint surfaces of sacro-iliac joint J oriented and aligned with openings 40, described above, of sacro-iliac implant 20. It is contemplated that cannula 366 may be employed to facilitate formation of such cavities by providing a preset alignment device for a surgical drill and/or tap.

Screw 46 is disposed with cannula 366, which is disposed in a preset orientation corresponding to the targeted trajectory for fastening of screw 46 with the components of the implant system and SI joint tissues, including bone. Cannula lock 361 is engaged to fix cannula 366 in a preset orientation. Screw 46 is delivered via cannula 366 to the sacro-iliac joint J into alignment with an opening 40 along a second trajectory $T_2$. Screw 46 is threaded with the joint surfaces of sacro-iliac joint J and/or implant 20 for fixation therewith to secure, stabilize and immobilize sacro-iliac joint J. This configuration tensions the joint ligaments of sacro-iliac joint J, spaces and supports sacro-iliac joint J to stabilize and treat a sacro-iliac disorder. It is envisioned that trajectory $T_1$ may be oriented perpendicular, parallel, angularly offset, offset, cruciate and/or staggered relative to trajectory $T_2$. The guide instrument releases implant 20 and screw 46 and is removed from the surgical site. It is contemplated that cannula arm 362 may include a screw holder for delivering and guiding a fastening element to the SI joint site. It is further contemplated that the arms 362, 372 may be arcuate and/or include bends.

Figure 9:
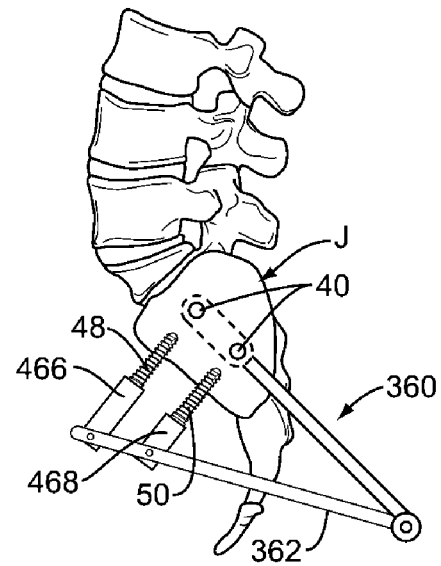
FIG. 9 is a side view of one embodiment of the implant system, partially shown in phantom, and the region shown in FIG. 8.

Referring to FIG. 9, in one embodiment similar to that described with regard to FIGS. 7 and 8, the implant system includes instrument 360, which includes cannula arm 362 having a plurality of cannulas, such as, for example, a first cannula arm 466 and a second cannula arm 468, each similar to cannula 366 described. The plurality of cannulas facilitate fixation of a plurality of fastening elements with the components of the implant system and/or SI joint tissues, including bone.

For example, a screw 48 is disposed with cannula 466, which is disposed in a preset orientation corresponding to the targeted trajectory for fastening of screw 48 with the components of the implant system and SI joint tissues, including bone. Screw 48 is delivered via cannula 466 to the sacro-iliac joint J into alignment with an opening 40 along the targeted trajectory. A screw 50 is disposed with cannula 468, which is disposed in a preset orientation corresponding to the targeted trajectory for fastening of screw 50 with the components of the implant system and SI joint tissues, including bone. Screw 50 is delivered via cannula 468 to the sacro-iliac joint J into alignment with an opening 40 along the targeted trajectory. Screws 48, 50 are threaded with the joint surfaces of sacro-iliac joint J and/or implant 20 for fixation therewith to secure, stabilize and immobilize sacro-iliac joint J.

Figure 10:
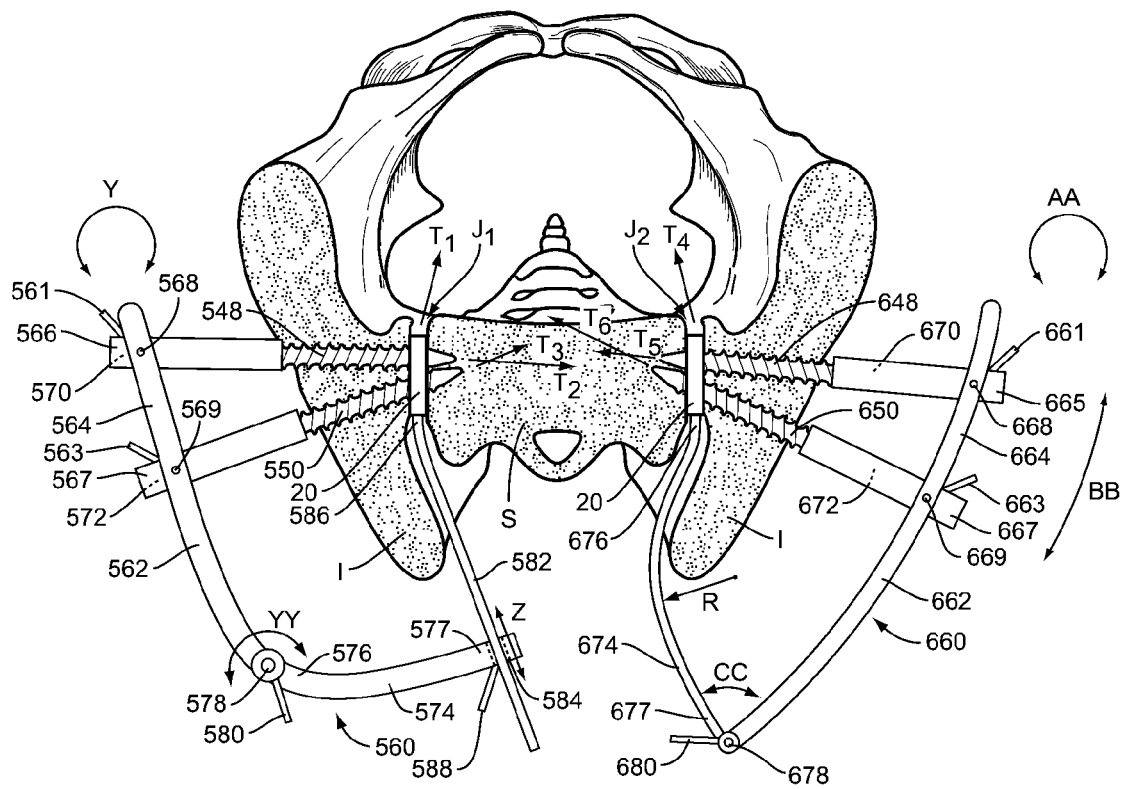
FIG. 10 is a plan view, in part cross section, of an implant system in accordance with the principles of the present disclosure and a sacro-iliac/ilio-pelvic region.

Referring to FIG. 10, in one embodiment similar to that described with regard to FIGS. 7 and 8, the implant system is employed with and includes an instrument 560 for treating a sacro-iliac joint disorder of a first sacro-iliac joint $J_1$. Instrument 560 includes a first arm, such as, for example, an elongated cannula arm 562 having an end portion 564 configured for connection to a first cannula 566 and a second cannula 567. Cannulas 566, 567 are movably connected to cannula arm 562 at pivot points 568, 569, respectively. Cannulas 566, 567 are each rotatable about pivot points 568, 569 through an angle of 360 degrees, in a clockwise or a counter clockwise direction as shown by arrows Y, relative to cannula arm 562. Cannulas 566, 567 are each rotatable to a predetermined orientation corresponding to a preselected trajectory for securing a fastening element with the components of the implant system and/or SI joint tissues, including bone.

Instrument 560 include cannula locks 561, 563 connected to cannula arm 562 adjacent cannulas 566, 567, respectively, to lock cannulas 566, 567 in predetermined orientations. Cannula 566 has a passageway 570 and is configured to receive and support a fastening element, such as, for example, screw 548. Cannula 566 facilitates delivery of screw 548 to joint $J_1$, as will be described. Cannula 567 has a passageway 572 and is configured to receive and support a fastening element, such as, for example, screw 550. Cannula 567 facilitates delivery of screw 550 to joint $J_1$, as will be described. It is envisioned that screws 548, 550 are configured for transarticular penetration of the tissues of joint $J_1$.

Instrument 560 includes a second arm 574 having a first end 576 and a second end 577. First end 576 is movably connected to cannula arm 562 at a pivot point 578. Second arm 574 is connected with cannula arm 562 such that cannula arm 562 is rotatable about pivot point 578 through an angle of 360 degrees, in a clockwise or a counter clockwise direction as shown by arrows YY, relative to second arm 574. Second arm 574 facilitates relative rotation of cannula arm 562 to further facilitate orientation of cannulas 566, 567 to a predetermined orientation corresponding to a preselected trajectory for securing a fastening element with the components of the implant system and/or SI joint tissues, including bone, as will be described. Instrument 560 includes a position lock, such as, for example, an arm lock 580 connected at pivot point 578 adjacent end 576 to lock cannula arm 562 in a predetermined orientation relative to second arm 574. It is contemplated that cannula 566 may be oriented perpendicular, parallel, angularly offset, offset, cruciate and/or staggered relative to cannula 567.

Instrument 560 includes a third arm, such as, for example, an implant arm 582 that is movably connected to second arm 574 adjacent second end 577. Second end 577 defines a cavity, such as, for example, a channel 584 configured for movable translation of implant arm 582 therein, in the direction shown by arrows Z relative to second arm 574. Implant arm 582 has an end 586 configured for detachable connection to an implant, such as, for example, implant 20. Implant arm 582 is slidable relative to second arm 574 such that implant 20 is deliverable in a predetermined orientation corresponding to a preselected trajectory for securing implant 20 between articular surfaces of joint $J_1$, as will be described. Instrument 560 includes a position lock, such as, for example, an arm lock 588 connected adjacent channel 584 to lock implant arm 582 in a predetermined orientation relative to second arm 574 and distance for depth of deployment of implant 20 within joint $J_1$.

In use, to treat the affected section of joint $J_1$, a medical practitioner conducts an investigation of the joint $J_1$ site to determine a location for implant 20 and fixation of screws 548, 550 in a cruciate orientation within the joint $J_1$ site. The location for implant 20 and fixation of screws 548, 550 are predetermined and targeted. The medical practitioner obtains access to a surgical site including sacro-iliac joint $J_1$ in any appropriate manner, similar to that described herein. A first trajectory $T_1$, corresponding to the predetermined location of implant 20, is defined for insertion and/or injection of sacro-iliac implant 20 within sacro-iliac joint $J_1$. Cannula arm 562, second arm 574 and implant arm 582 are disposed in a preset orientation according to the predetermined target locations for implant 20 and screws 548, 550. Implant 20 is connected to end 586 and implant 20 is inserted via the protected passageway, described above, along the defined trajectory $T_1$, in the direction shown by arrow Z, into sacro-iliac joint $J_1$. A cavity of sacro-iliac joint $J_1$ is prepared along trajectory $T_1$ for disposal of sacro-iliac implant 20.

Sacro-iliac implant 20 is manipulated to engage opposing articular surfaces, described above, of the SI joint $J_1$. Sacro-iliac implant 20 is disposed with sacro-iliac joint $J_1$ for treating the sacro-iliac joint disorder in an orientation for engaging and spacing apart the respective opposing articular surfaces. Implant 20 is secured within joint $J_1$ to stabilize and immobilize portions of the sacrum and ilium of sacro-iliac joint $J_1$.

Upon placement of sacro-iliac implant 20, lock 588 is engaged to maintain position of implant 20 within sacro-iliac joint $J_1$. Cavities are tapped and/or drilled in the joint surfaces of sacro-iliac joint $J_1$ oriented and aligned with openings 40 (not shown) of sacro-iliac implant 20. It is contemplated that cannulas 566, 567 may be employed to facilitate formation of such cavities by providing a preset alignment device for a surgical drill and/or tap.

Cannula arm 562 is disposed in a preset orientation corresponding to the targeted trajectory for fastening of screws 548, 550 with the components of the implant system and SI joint tissues, including bone. Lock 580 is engaged to fix cannula arm 562 in a preset orientation. Screws 548, 550 are disposed with cannulas 566, 567, which are disposed in a preset orientation corresponding to the targeted trajectory for fastening of screws 548, 550 with the components of the implant system and SI joint tissues. Cannula locks 561, 563 are engaged to fix cannulas 566, 567 in a preset orientation. Screws 548, 550 are delivered via cannulas 566, 567 to the sacro-iliac joint $J_1$ into alignment with openings 40 along a second trajectory $T_2$ and a third trajectory $T_3$, respectively. Screws 548, 550 are threaded with the joint surfaces of sacro-iliac joint $J_1$ and/or implant 20 for fixation therewith to secure, stabilize and immobilize sacro-iliac joint $J_1$. This configuration tensions the joint ligaments of sacro-iliac joint $J_1$, spaces and supports sacro-iliac joint $J_1$ to stabilize and treat a sacro-iliac disorder. It is envisioned that the defined trajectories may be oriented perpendicular, parallel, angularly offset, offset, cruciate and/or staggered relative to the other defined trajectories. The guide instrument 560 releases implant 20 and screws 548, 550 and is removed from the surgical site. It is contemplated that the arms 562, 574 and 582 may be arcuate, linear and/or include bends.

The implant system is also employed with and includes an instrument 660, similar to instrument 560 described above, for treating a sacro-iliac joint disorder of a second sacro-iliac joint $J_2$. Instrument 660 includes a first arm, such as, for example, a cannula arm 662 having an end portion 664 configured for connection to a first cannula 665 and a second cannula 667. Cannulas 665, 667 are movably connected to cannula arm 662 at pivot points 668, 669, respectively. Cannulas 665, 667 are each rotatable about pivot points 668, 669 through an angle of 360 degrees, in a clockwise or a counter clockwise direction as shown by arrows AA, relative to cannula arm 662. Cannulas 665, 667 and pivot points 668, 669 are movable, in the direction shown by arrows BB, within a slot (not shown) of cannula arm 662 to facilitate slidable translation of cannulas 665, 667 relative to cannula arm 662. It is contemplated that cannulas 665, 667, individually or collectively, can be preset in one or multiple orientations through the angle of 360 degrees and/or along the slot of cannula arm 662.

Cannulas 665, 667 are each configured for translation and/or rotation to a predetermined orientation corresponding to a preselected trajectory for securing a fastening element with the components of the implant system and/or SI joint tissues, including bone. Instrument 660 include cannula locks 661, 663 connected to cannula arm 662 adjacent cannulas 665, 667, respectively, to lock cannulas 665, 667 in predetermined orientations, which include a translation orientation and/or a rotation orientation relative to cannula arm 662. Cannula 665 has a passageway 670 and is configured to receive and support a fastening element, such as, for example, screw 648. Cannula 665 facilitates delivery of screw 648 to joint $J_2$, as will be described. Cannula 667 has a passageway 672 and is configured to receive and support a fastening element, such as, for example, screw 650. Cannula 667 facilitates delivery of screw 650 to joint $J_2$, as will be described. It is envisioned that screws 648, 650 are configured for transarticular penetration of the tissues of joint $J_2$.

Instrument 660 includes a second arm, such as, for example, a swing arm 674 having a first end 676 and a second end 677. First end 676 is configured for detachable connection to an implant, such as, for example, implant 20. Swing arm 674 is movably connected to cannula arm 662 at a pivot point 678. Swing arm 674 is rotatable about pivot point 678 through an angle of 360 degrees, in a clockwise or a counter clockwise direction as shown by arrows CC, relative to cannula arm 662. Instrument 660 includes a position lock, such as, for example, an arm lock 680 connected at pivot point 678 adjacent end 677 to lock swing arm 674 in a predetermined orientation relative to cannula arm 662. Swing arm 674 has an arcuate configuration including a radius R according to the requirements of a particular predetermined orientation and/or application. It is contemplated that radius R may be in a range of approximately 1-24 inches, and preferably in a range of approximately 3-15 inches.

Swing arm 674 and cannula arm 662 are relatively rotatable such that implant 20 is rotatable to a predetermined orientation corresponding to a preselected trajectory for securing implant 20 between articular surfaces of a SI joint $J_2$, and/or further facilitate orientation of cannulas 665, 667 to predetermined orientations corresponding to a preselected trajectory for securing a fastening element with the components of the implant system and/or SI joint tissues, including bone, as will be described.

In use, to treat the affected section of joint $J_2$, a medical practitioner conducts an investigation of the joint $J_2$ site to determine a location for implant 20 and fixation of screws 648, 650 within the joint $J_2$ site. The location for implant 20 and fixation of screws 648, 650 are predetermined and targeted. The medical practitioner obtains access to a surgical site including sacro-iliac joint $J_2$ in any appropriate manner, similar to that described herein. A first trajectory $T_4$, corresponding to the predetermined location of implant 20, is defined for insertion and/or injection of sacro-iliac implant 20 within sacro-iliac joint $J_2$. Cannula arm 662 and swing arm 674 are disposed in a preset orientation according to the predetermined target locations for implant 20 and screws 648, 650. Implant 20 is connected to end 676 and implant 20 is inserted via the protected passageway, described above, along the defined trajectory $T_4$ into sacro-iliac joint $J_2$. A cavity of sacro-iliac joint $J_2$ is prepared along trajectory $T_4$ for disposal of sacro-iliac implant 20.

Sacro-iliac implant 20 is manipulated to engage opposing articular surfaces, described above, of the SI joint $J_2$. Sacro-iliac implant 20 is disposed with sacro-iliac joint $J_2$ for treating the sacro-iliac joint disorder in an orientation for engaging and spacing apart the respective opposing articular surfaces. Implant 20 is secured within joint $J_2$ to stabilize and immobilize portions of the sacrum and ilium of sacro-iliac joint $J_2$.

Upon placement of sacro-iliac implant 20, lock 680 is engaged to maintain position of implant 20 within sacro-iliac joint $J_2$. Cavities are tapped and/or drilled in the joint surfaces of sacro-iliac joint $J_2$ oriented and aligned with openings 40 (not shown) of sacro-iliac implant 20. It is contemplated that cannulas 665, 667 may be employed to facilitate formation of such cavities by providing a preset alignment device for a surgical drill and/or tap.

Screws 648, 650 are disposed with cannulas 665, 667, which are disposed in a preset orientation corresponding to the targeted trajectory for fastening of screws 648, 650 with the components of the implant system and SI joint tissues. Cannula locks 661, 663 are engaged to fix cannulas 665, 667 in a preset orientation. Screws 648, 650 are delivered via cannulas 665, 667 to the sacro-iliac joint $J_2$ into alignment with openings 40 along a second trajectory $T_5$ and a third trajectory $T_6$, respectively. Screws 648, 650 are threaded with the joint surfaces of sacro-iliac joint $J_2$ and/or implant 20 for fixation therewith to secure, stabilize and immobilize sacro-iliac joint $J_2$. This configuration tensions the joint ligaments of sacro-iliac joint $J_2$, and spaces and supports sacro-iliac joint $J_2$ to stabilize and treat a sacro-iliac disorder. It is envisioned that cannulas 665, 667 and/or the defined trajectories may be oriented perpendicular, parallel, angularly offset, offset, cruciate and/or staggered relative to the other defined trajectories. Guide instrument 660 releases implant 20 and screws 648, 650 and is removed from the surgical site. It is contemplated that the arm 674 may be arcuate, linear and/or include bends. It is further contemplated that arm 662 may be linear and/or include bends.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A sacro-iliac implant delivery instrument comprising:
a first arm having a first end portion connected to a first cannula at a first pivot, the first cannula being rotatable about the first pivot relative to the first arm and being configured for support of a fastening element; and
a second arm being connected to the first arm at a second pivot, the second arm being rotatable about the second pivot relative to the first arm and being configured for detachable connection to a sacro-iliac implant,
the second arm and the first cannula being configured for rotation relative to the first arm to a preset orientation such that the second arm is disposed along a first predetermined trajectory for delivering the sacro-iliac implant and the first cannula is disposed along a second predetermined trajectory for delivering the fastening element in alignment with the sacro-iliac implant for transarticular fixation,
a third arm configured for translation relative to the second arm to the preset orientation which includes disposal of the third arm along the first predetermined trajectory; and
a lock disposed adjacent the cavity and configured to fix the third arm along the first predetermined trajectory in the preset orientation.

2. A sacro-iliac implant delivery instrument according to claim 1, wherein the first cannula is configured for translation relative to the first arm.

3. A sacro-iliac implant delivery instrument according to claim 1, further comprising a lock disposed adjacent the first end portion of the first arm and being configured to fix the first cannula along the second predetermined trajectory in the preset orientation.

4. A sacro-iliac implant delivery instrument according to claim 1, wherein the first arm is connected to a second cannula at a third pivot, the second cannula being rotatable about the third pivot relative to the first arm and being configured for support of a fastening element.

5. A sacro-iliac implant delivery instrument according to claim 4, wherein the second cannula is configured for rotation relative to the first arm to the preset orientation, which includes disposal of the second cannula in a third predetermined trajectory for delivering the fastening element in alignment with the sacro-iliac implant for transarticular fixation.

6. A sacro-iliac implant delivery instrument according to claim 5, further comprising a lock disposed adjacent the second cannula and being configured to fix the second cannula along the third predetermined trajectory in the preset orientation.

7. A sacro-iliac implant delivery instrument according to claim 1, further comprising a lock disposed adjacent the second pivot and being configured to fix the second arm along the first predetermined trajectory in the preset orientation.

8. A sacro-iliac implant delivery instrument according to claim 1, wherein the second arm includes a third arm configured for detachable connection with the sacro-iliac implant, the second arm defining a cavity configured for relative slidable translation of the third arm therein.

9. A sacro-iliac implant system comprising:
a first sacro-iliac implant defining at least one opening;
at least one fastening element configured for disposal in the at least one opening; and
a first sacro-iliac implant delivery instrument including:
a first arm having a first end portion connected to a first cannula at a first pivot, the first cannula being rotatable about the first pivot relative to the first arm and being configured for translation relative to the first arm, the first cannula being configured for support of a fastening element; and
a second arm being connected to the first arm at a second pivot, the second arm being rotatable about the second pivot relative to the first arm and being configured for detachable connection to the first sacro-iliac implant,
the second arm being configured for rotation and the first cannula being configured for rotation and translation, relative to the first arm, to a preset orientation such that the second arm is disposed along a first predetermined trajectory for delivering the sacro-iliac implant and the first cannula is disposed along a second predetermined trajectory for delivering the fastening element in alignment with the first sacro-iliac implant for transarticular fixation.

10. A sacro-iliac implant delivery instrument according to claim 9, further comprising:
a second sacro-iliac implant defining at least one opening;

the at least one fastening element including a plurality of fastening elements; and a second sacro-iliac implant delivery instrument including:

a first arm of the second instrument being connected to a first cannula of the second instrument, the first cannula of the second instrument being rotatable relative to the first arm of the second instrument and being configured for support of a fastening element;

a second arm of the second instrument being connected to the first arm of the second instrument, the second arm of the second instrument being rotatable relative to the first arm of the second instrument; and a third arm being connected to the second arm of the second instrument and configured for relative slidable translation within a cavity of the second arm of the second instrument, the third arm being configured for detachable connection with the second sacro-iliac implant, the second arm and the first cannula of the second instrument being configured for rotation relative to the first arm of the second instrument, and the third arm being configured for translation relative to the second arm of the second instrument, to a preset orientation such that the third arm is disposed along a third predetermined trajectory for delivering the second sacro-iliac implant and the first cannula of the second instrument is disposed along a fourth predetermined trajectory for delivering the fastening element in alignment with the second sacro-iliac implant for transarticular fixation.

11. A sacro-iliac implant delivery instrument according to claim 10, further comprising a lock disposed adjacent the cavity and being configured to fix the third arm along the third predetermined trajectory in the preset orientation.

12. A sacro-iliac implant delivery instrument according to claim 9, wherein the first arm is connected to a second cannula, the second cannula being rotatable about the first arm and being configured for support of a fastening element.

13. A sacro-iliac implant delivery instrument according to claim 12, wherein the second cannula is configured for rotation relative to the first arm to the preset orientation, which includes disposal of the second cannula in a third predetermined trajectory for delivering the fastening element in alignment with the second sacro-iliac implant for transarticular fixation.

14. A sacro-iliac implant delivery instrument according to claim 13, further comprising a lock disposed adjacent the second cannula and being configured to fix the second cannula along the third predetermined trajectory in the present orientation.

15. A sacro-iliac implant delivery instrument according to claim 9, further comprising a lock disposed adjacent the first end portion of the first arm and being configured to fix the first cannula along the second predetermined trajectory in the preset orientation.

16. A method for treating a sacro-iliac joint, the method comprising the steps of:

providing a first sacro-iliac implant defining at least one opening;

providing at least one fastening element;

providing a first sacro-iliac implant delivery instrument including:

a first arm connected to a first cannula, the first cannula being rotatable relative to the first arm and being configured for support of a fastening element; and a second arm being connected to the first arm, the second arm being rotatable relative to the first arm and being configured for detachable connection to a first sacro-iliac implant, preselecting a target location within the sacro-iliac joint for disposal of the first sacro-iliac implant;

configuring the first sacro-iliac delivery instrument in a preset orientation such that the second arm is disposed along a first predetermined trajectory for delivering the first sacro-iliac implant and the first cannula is disposed along a second predetermined trajectory for delivering the fastening element in alignment with the sacro-iliac implant for transarticular fixation;

delivering the first sacro-iliac implant within the sacro-iliac joint with the second arm disposed in the preset orientation;

delivering the at least one fastening element within the sacro-iliac joint with the first cannula disposed in the preset orientation;

inserting the at least one fastening element within the at least one opening of the first sacro-iliac implant; and securing the at least one fastening element in the transarticular fixation.

17. A method according to claim 16, further comprising a step of providing a second cannula connected to the first arm, the second cannula being rotatable relative to the first arm and being configured for support of a fastening element, wherein the second cannula is configured for rotation relative to the first arm to the preset orientation, which includes disposal of the second cannula in a third predetermined trajectory for delivering the fastening element in alignment with the first sacro-iliac implant for transarticular fixation.

18. A method according to claim 17, further comprising the step of providing a sacro-iliac implant delivery instrument wherein the second arm includes a third arm configured for detachable connection with the sacro-iliac implant, the second arm defining a cavity configured for relative slidable translation of the third arm therein, wherein the third arm is configured for translation relative to the second arm to the preset orientation, which includes disposed of the third arm along the first predetermined trajectory.

* * * * *